(12) United States Patent
Deferm et al.

(10) Patent No.: US 10,429,322 B2
(45) Date of Patent: Oct. 1, 2019

(54) SENSOR FOR NON-DESTRUCTIVE CHARACTERIZATION OF OBJECTS

(71) Applicant: HAMMER-IMS, Hasselt (BE)

(72) Inventors: Noël Deferm, Beverlo (BE); Tom Redant, Alken (BE); Wim Dehaene, Kessel-Lo (BE); Patrick Reynaert, Boutersem (BE)

(73) Assignee: HAMMER-IMS, Hasselt (BE)

( * ) Notice: Subject to any disclaimer, the term of this patent is extended or adjusted under 35 U.S.C. 154(b) by 99 days.

(21) Appl. No.: 15/735,353

(22) PCT Filed: Jun. 13, 2016

(86) PCT No.: PCT/EP2016/063484
§ 371 (c)(1),
(2) Date: Dec. 11, 2017

(87) PCT Pub. No.: WO2016/198690
PCT Pub. Date: Dec. 15, 2016

(65) Prior Publication Data
US 2018/0180557 A1    Jun. 28, 2018

(30) Foreign Application Priority Data
Jun. 12, 2015   (GB) .................................. 1510234.6

(51) Int. Cl.
*G01N 22/02*   (2006.01)
*G01N 33/34*   (2006.01)
(Continued)

(52) U.S. Cl.
CPC .............. *G01N 22/02* (2013.01); *G01B 7/06* (2013.01); *G01B 11/06* (2013.01); *G01N 21/3581* (2013.01); *G01N 21/86* (2013.01); *G01N 21/89* (2013.01); *G01N 21/8915* (2013.01); *G01N 21/8983* (2013.01); *G01N 33/346* (2013.01); *G01N 33/367* (2013.01); *G01N 2021/8663* (2013.01); *G01N 2021/8917* (2013.01)

(58) Field of Classification Search
CPC .......... G01W 1/16; G01W 1/10; G01R 27/28; G01R 29/26; G01R 29/0842; H04B 1/1027
USPC ................ 324/620, 346, 333, 334, 338, 339
See application file for complete search history.

(56) References Cited

U.S. PATENT DOCUMENTS 4,326,163 A    4/1982   Brooke
4,812,739 A    3/1989   Swanson
(Continued)

FOREIGN PATENT DOCUMENTS

DE   102011002413 A1   7/2012
EP       1703275 A1   9/2006
WO    2009082820 A1   7/2009

OTHER PUBLICATIONS

Nyfors et al., "Industrial Microwave Sensors", Artech House, Jan. 1, 1989, 3 Pages.
(Continued)

*Primary Examiner* — Giovanni Astacio-Oquendo
(74) *Attorney, Agent, or Firm* — Workman Nydegger

(57) ABSTRACT

The present invention relates to a millimeter or terahertz wave sensor for providing inline inspection, preferably including but not limited to continuous monitoring of objects, for example thin sheet dielectric material.

20 Claims, 10 Drawing Sheets

(51) Int. Cl.
    *G01N 33/36*     (2006.01)
    *G01N 21/86*     (2006.01)
    *G01N 21/3581*     (2014.01)
    *G01N 21/89*     (2006.01)
    *G01N 21/898*     (2006.01)
    *G01B 7/06*     (2006.01)
    *G01B 11/06*     (2006.01)

(56) References Cited

U.S. PATENT DOCUMENTS

| | | | | |
|---|---|---|---|---|
| 5,808,449 | A | * | 9/1998 | Hirayama ............ H02J 3/46 |
| | | | | 307/73 |
| 5,886,534 | A | | 3/1999 | Bakhtiari et al. |
| 7,408,268 | B1 | * | 8/2008 | Nocentini ............ H02J 3/38 |
| | | | | 307/16 |
| 2003/0146767 | A1 | | 8/2003 | Steele et al. |
| 2011/0068631 | A1 | * | 3/2011 | Roscoe ............ H02J 3/38 |
| | | | | 307/69 |

OTHER PUBLICATIONS

Great Britain Search Report from GB Application No. GB1510234.6, dated Jul. 14, 2015.
International Search Report and Written Opinion from PCT Application No. PCT/EP2016/063484, dated Aug. 4, 2016.

\* cited by examiner

SENSOR FOR NON-DESTRUCTIVE CHARACTERIZATION OF OBJECTS

FIELD OF THE INVENTION

The present invention relates to millimeter or terahertz wave sensing. More particularly it relates to a sensor and method for sensing allowing for example inline inspection (like e.g. inspection in production lines), preferably including but not limited to continuous monitoring of objects, for example thin sheet-like dielectric materials, such as fabric, paper, plastic and other dielectric objects with respect to macroscopic and/or microscopic properties such as density, weight, thickness, homogeneity, internal flaws, structure (like e.g. 2D topology), porosity, moisture content, dielectric conditions, and state of cure. More specifically the invention relates to a sensor and instrument system using a signal comprising at least two tones wherein preferably the at least two tones of the signal are symmetrically spaced around a carrier frequency.

BACKGROUND OF THE INVENTION

Several methods are known in the art for sensing thicknesses or weights of materials. These can be based on nuclear radiation, X-ray methods, optical methods based on laser triangulation, acoustic methods based on time-of-flight, etc.

Due to the rising importance of millimeter-wave communication technology in the field of consumer electronics, attention to millimeter-waves and terahertz signals has been shown for sensing applications. Millimeter-wave and terahertz based sensing applications have certain advantages with respect to the industry-standard nuclear based techniques. Radioactive solutions have high indirect cost-of-ownership due to the harmfulness of the used radiation type, whereas millimeter-waves and terahertz radiation is non-ionizing. In addition, current trends in safety regulations (like for instance in Europe) are guiding consumers to be critical while obtaining licenses for new nuclear systems which are based on ionizing radiation.

The corresponding wavelengths are at maximum a few millimeters, yielding interesting applications for precise and accurate sensing. An important condition is that the signal's phase values are sufficiently reliable to use them as the physical parameter on which the sensing concept is based.

U.S. Pat. No. 5,886,534 provides a millimeter wave sensor for non-destructive inspection of thin sheet dielectric materials. To enable the latter US'534 uses a single antenna which generates a signal which is reflected from the surface of the thin sheet dielectric material. This means that for cases where high amounts of reflections on the thin sheet dielectric material occurs (e.g. when the material has a high index of refraction), the sensor mainly measures the surface state of the thin sheet.

DE102011002413 describes a backscatter imaging device comprising a lock-in amplifier that generates an output signal by correlating an intermediate frequency signal with a correlation signal. DE'413 uses a heteronymous receiver or conventional correlation reception systems which generate a received signal based on radiation emitted from a transmitter. For this purpose, the device comprises a transmitter for emitting a radiation based on a carrier signal having a carrier frequency. The device generates a received signal and an intermediate frequency signal by mixing the received signal with a tuning signal, wherein the tuning frequency is different from the carrier frequency.

Hence there remains a need for millimeter wave sensing methods and devices.

SUMMARY OF THE INVENTION

It is an object of embodiments of the present invention to provide methods and devices to achieve good sensing based on millimeter-wave and terahertz signals.

It is an advantage of embodiments of the present invention that good solutions and implementations for estimating an electric length of an object, a medium or an object in a medium are provided. The electric length of this object, medium or object in a medium can then be related to physical dimensions of objects (i.e. lengths, thickness, unevenness, etc.).

The above objective is accomplished by a method and device according to the present invention.

It is an advantage of embodiments of the present invention to provide a good, e.g. improved, device for estimating an electric length of an object and enabling derivation of the physical length of a certain object.

It is an advantage of embodiments of the present invention that a wireless sensing device is provided enabling a non-invasive or contactless characterization of an object placed in an electrically well-defined medium. Characterization of an object may for instance be a thickness, weight or surface roughness of a certain measurement spot on an object, like e.g. a test sample. When multiple measurement spots are combined, this advantageously results in a topographical 2D map.

It is an advantage of embodiments of the present invention that millimeter or terahertz waves are used, which are non-ionizing and thus can penetrate many materials and biological tissue without an ionizing effect. Millimeter waves are non-nuclear and non-radioactive. It is an advantage of embodiments of the present invention that these may comply easy with legislation to guarantee personnel safety and security.

It is an advantage of embodiments of the present invention that precise and accurate sensing solutions are provided.

It is an advantage of embodiments of the present invention that millimeter wave or terahertz sensors are provided that can be used for inline inspection of objects, for example of thin sheet dielectrics.

It is an advantage of embodiments of the present invention that devices are provided which are compact and have a small size antenna, and which are self-calibrating.

It is an advantage of embodiments of the present invention that various sorts of materials (for instance, synthetics, paper, webs, biological materials, etc.) can be characterized and sensed. Embodiments of the present invention can advantageously be applied in the field of industrial sensing of parameters of flat sheet-like or film-like surfaces while being produced or processed. Example industries where these materials need to be inspected are for example the paper industry, the textile industry, the synthetics industry (foams, films, sheets, PCBs, filters, tapes, etc.), the composite industry, the glass industry, the rubber industry, glass wool and mineral wool production, rock wool production. In these industries, either one or both of the following parameters are critical: sheet weights and sheet thicknesses. A sheet as referred to in embodiments of the present invention may be a solid sheet, a porous sheet or a web like sheet.

It is an advantage of embodiments of the present invention that the device can be used to measure, and more specifically estimate, a thickness of a sheet material in inline production environments. In further embodiment a thickness of coating provided on a carrier can be measured using embodiments of the present invention. The technique can thus be applied to continuously keep track of material thickness and prevent production errors resulting in production downtime and production material losses. In such an application, the millimeter waves or terahertz signals require sufficient penetration within an object, preferably a sheet material. Sheet materials could be one of the following products: paper, textiles, non-wovens, plastic sheets and films, foams, glass, rubber, glass-reinforced plastics, specific biological material, PCBs, filter materials, tapes, glass wool, mineral wool, etc. However, it is to be noted that embodiments of the present invention are not limited to the sheet types listed here.

Embodiments of the present invention provide a powerful alternative for today's nuclear measuring equipment, which are discouraged by governments. In addition, embodiments of the present invention offer the following advantages: (1) Highly accurate thickness and basis weight measurement, (2) advanced scanning of materials in cross machine direction, (3) material profile measurement up to speeds of 250 meter per minute and (4) insensitive to light and environment and robust to production floor conditions.

In a first aspect the present invention provides methods for estimating a specification of a medium or an object in a medium, said method comprising:

generating a transmitting signal ($T_x$), wherein the transmitting signal ($T_x$) is provided by using a periodic baseband input signal having a frequency which is mixed with a first frequency reference ($f_r$) resulting in a signal comprising at least two tones;

transmitting said transmitting signal trough said object and/or medium;

receiving the resulting transmitted signal, transmitted through the object and/or medium, resulting in a received signal ($R_x$) wherein said received signal comprises a phase shift ($\varepsilon_0$);

characterized in that the received signal ($R_x$) comprising a phase shift ($\varepsilon_0$) is mixed with the first frequency reference ($f_r$) resulting in that the transmitting signal ($T_x$) is generated with and the received signal ($R_x$) is processed with the same frequency reference and therefore share the first frequency reference ($f_r$), and estimating the phase shift ($\Phi_0$) and relating the estimated phase shift to the medium's and/or object's specification such to estimate the medium's and/or object's specification.

It is an advantage of embodiments of the present invention that the transmitting and receiving signal share the same frequency reference ($f_r$). More specifically in embodiments of the present invention the up and down conversion are performed by the same shared frequency ($f_r$). It is an advantage of embodiments of the present invention that a shared or same frequency reference provides a reliable sensor value. It is a further advantage of embodiments of the present invention that possible drift in measurements is reduced to a minimum since frequencies for the up and down conversion cannot drift with respect to each other, which reduces calibration overhead.

A model may be used to relate the estimated phase shift to the medium's and/or object's specification, wherein the model can be a mathematical expression or an empirically-obtained look-up table.

In preferred embodiments mixing of the received signal ($R_x$) with the frequency reference ($f_r$) converts the received signal ($R_x$) in an in-phase (I) and/or quadrature (Q) component.

Embodiments of a method according to the present invention further may comprise a digitizing step, wherein said digitizing step comprises digitizing the in-phase (I) and/or quadrature (Q) component. Preferably said digitizing step comprising providing a second reference frequency ($f_r'$).

In preferred embodiments, the second reference frequency ($f_r'$) is derived from the first reference frequency ($f_r$), or vice versa, or both (the first and second) can be derived from a third reference frequency ($f_r''$).

In preferred embodiments the specification of the object estimated is a thickness and/or weight of the object or a coating thickness of the object or a parameter indicative of the dielectric state of the object and/or the refractive index and/or dielectric constant. Preferably a thickness of the object is estimated using amplitude values of the in-phase component, the quadrature component or a combination of both.

In preferred embodiment a method according to the present invention further comprises a calibration or tuning step. The calibration step may comprise tuning a delay of the received signal electrically within the receiver. The calibration step may comprise tuning or sweeping a total distance between a means for generating a transmitting signal and a means for receiving the receiving signal (D) mechanically.

The calibration step may comprise tuning or sweeping a total distance between a means for generating a transmitting signal and a means for reflecting (D') mechanically.

The calibration step may comprise angular tuning, said angular tuning comprising fine-tuning an angle of a signal path to an optimal value such as to prevent reflection towards a means for generating a transmitting signal.

The method may comprise a monitoring step, wherein environmental parameters of the object in which the estimation is performed are obtained.

In further preferred embodiments the object sensed is a sheet material having a thickness in the micrometer to centimeter range.

In yet further preferred embodiments the object and medium are adapted to be at least partially transparent for light and/or at least partially transparent for electromagnetic waves.

In preferred embodiments the first reference frequency ($f_r$) is in the order of 0.1 MHz to 3e12 Hz, preferably 1 GHz to 300 GHz and more specifically 10 GHz to 150 GHz or 30 GHz to 300 Ghz.

It is an advantage of embodiments of the present invention that electro-magnetic waves comprising said first frequency can at least partially penetrate through a range of non-metallic materials. The high frequencies enable high precision distance sensing, or sensing quantities such as material thickness or weight (e.g. basis-weight) that optical measuring systems cannot sense.

It is an advantage of embodiments of the present invention that transparent and opaque (amongst others) materials can be sensed. In addition, materials in any color as well as rough and shiny surfaces. An example of such materials may be for example: ABS, (dry) paper, EVA, glass, glass-fiber/epoxy-resin based composite, HDPE, LDPE, PA (Nylon), PE, PMMA, PMP, Polycarbonate, Polyethylene-based materials, PP, PPS, PVC-coated paper, PVDF and glass and mineral woll.

In a second aspect, the present invention provides a computer program product for, if implemented on a control unit, performing a method according to the first aspect of the present invention.

In a third aspect, the present invention provides a data carrier storing a computer program product according to the seventh aspect of the present invention. The term "data carrier" is equal to the terms "carrier medium" or "computer readable medium", and refers to any medium that participates in providing instructions to a processor for execution. Such a medium may take many forms, including but not limited to, non-volatile media, volatile media, and transmission media. Non-volatile media include, for example, optical or magnetic disks, such as a storage device which is part of mass storage. Volatile media include dynamic memory such as RAM. Common forms of computer readable media include, for example, a floppy disk, a flexible disk, a hard disk, magnetic tape, or any other magnetic medium, a CD-ROM, any other optical medium, punch cards, paper tapes, any other physical medium with patterns of holes, a RAM, a PROM, an EPROM, a FLASH-EPROM, any other memory chip or cartridge, a carrier wave as described hereafter, or any other medium from which a computer can read. Various forms of computer readable media may be involved in carrying one or more sequences of one or more instructions to a processor for execution. For example, the instructions may initially be carried on a magnetic disk of a remote computer. The remote computer can load the instructions into its dynamic memory and send the instructions over a telephone line using a modem. A modem local to the computer system can receive the data on the telephone line and use an infrared transmitter to convert the data to an infrared signal. An infrared detector coupled to a bus can receive the data carried in the infra-red signal and place the data on the bus. The bus carries data to main memory, from which a processor retrieves and executes the instructions. The instructions received by main memory may optionally be stored on a storage device either before or after execution by a processor. The instructions can also be transmitted via a carrier wave in a network, such as a LAN, a WAN or the internet. Transmission media can take the form of acoustic or light waves, such as those generated during radio wave and infrared data communications. Transmission media include coaxial cables, copper wire and fibre optics, including the wires that form a bus within a computer.

In a fourth aspect, the present invention provides in transmission of a computer program product according to the second aspect of the present invention over a network.

In a fifth aspect the present invention provides systems for characterizing a medium or an object in the medium, said device comprising:

at least one means for generating a transmitting signal for transmitting said signal through the medium or the object in the medium;

at least one means for receiving the transmitted signal transmitted through the medium or the object in the medium; and a controller programmed for performing a method according to the first aspect and run the computational part of the embodiments of the invention (algorithm).

It also may relate to a system for characterizing a medium or an object in a medium, said system comprising:

at least one means for generating a transmitting signal provided by using a periodic baseband input signal having a frequency which is mixed with a first frequency reference ($f_r$) resulting in a signal comprising at least two tones, for transmitting the transmitting signal through the medium or the object in the medium;

at least one means for receiving the transmitted signal, transmitted through the medium or the object in the medium, thus obtaining a received signal ($R_x$), the received signal comprising a phase shift ($\varepsilon_0$); and a control unit programmed for mixing the received signal ($R_x$) with the first frequency reference ($f_r$) resulting in that the transmitting signal ($T_x$) is generated with and the received signal ($R_x$) is mixed with the same frequency therefore sharing the first frequency reference ($f_r$), estimating the phase shift ($\Phi_0$) and relating the estimated phase shift to the medium's and/or object's specification such to estimate the medium's and/or objects specification. In preferred embodiments the system further may comprise a transmitter and receiver, wherein said transmitter and receiver comprise the electronics for preparing a signal for the use as transmitting signal and for processing a receiving signal respectively. In preferred embodiments the transmitter or receiver comprises the electronics which are adapted to perform respectively the up- or down converting, according to embodiments of the present invention. Moreover, both receiver and transmitter may additionally contain amplification stages. In embodiments a plurality of means for generating a transmitting signal can be connected to one transmitter or a plurality of transmitters. In other embodiments a plurality of means for receiving can be connected to one receiver or a plurality of receivers. In further preferred embodiments the means for generating a transmitting signal is provided adjacent, e.g. in front or back, of the transmitter and where the means for receiving is provided adjacent to the receiver. In preferred embodiments the means for generating a transmitting signal and receiving are antenna means, for example aerials or transducers designed to respectively transmit or receive electromagnetic waves.

In embodiments the system also may comprise a digital platform configured for providing a periodic baseband input signal having a frequency.

In embodiments the system may also comprise a data acquisition device adapted to digitize the received signal. In preferred embodiments the data acquisition device is adapted to sample the received signal preferably after said the received signal is multiplied with the frequency reference ($f_r$).

The transmitter may be adapted for mixing the periodic baseband input signal with a first frequency reference ($f_r$) resulting in a signal comprising at least two tones.

The receiver may be adapted for mixing the signal with the first frequency reference ($f_r$) resulting in that the transmitting signal ($T_x$) is generated and the received signal ($R_x$) is processed by the same frequency reference ($f_r$).

In preferred embodiments at least one means for generating a transmitting signal and at least one means for receiving are provided opposite each other defining an opening with a distance (D).

In alternative preferred embodiments the means for receiving and transmitting are positioned adjacent each other and further comprising at least one means for reflecting the transmitted signal, wherein the receiving and transmitting means are positioned, at a same distance, opposite to the means for reflecting defining an opening with a distance (D').

In preferred embodiments the defined openings (D, D') can be adjusted.

In further preferred embodiments the system is provided on a frame and more specifically C, U or O-frame, where the frame is preferably a metal frame.

In further alternative embodiments, only the means for receiving and transmitting, and optionally protecting or absorbing means for said means for receiving and transmitting, are provided on a frame and more specifically a C, U or O-frame.

In further preferred embodiments, at least one radio-absorbing material is provided nearby the receiving means, the transmitting means or even both.

In further preferred embodiments, the system is further adapted to combine information obtained from other sensors, such to enable:

a more reliable measurement, and/or canceling out a cross-sensitivity to other object properties other than the one within the interest of the application, and/or more object properties than can be measured by means of the standalone system.

The system may comprise a plurality of pairs of means for generating a transmitting signal and receiving means wherein the plurality of means for generating a transmitting signal and receiving means are provided on a frame defining an opening (D, D') which can be adjusted.

The at least one means for generating a transmitting signal and receiving means may be adapted to move in a same direction with respect to an object when in use.

The device may comprise an O-frame comprising a plurality of sensor head pairs, each pair comprising means for generating a transmitting signal and receiver means, and each pair separated by a distance D.

The present invention also relates to a system comprising a plurality of pairs of transmitting and receiving means, wherein the plurality of means for generating a transmitting signal and receiving means are provided on a frame defining an opening (D, D') which can be adjusted; a control unit (510) for performing a method as described above. In a sixth aspect the present invention provides use of a system according to embodiments of the invention for measuring and estimating a thickness and/or weight of an object.

In one embodiment, the invention also relates to a method for estimating a specification of an object in a medium, said method comprising:

generating a transmitting signal ($T_x$), wherein the transmitting signal ($T_x$) is provided by using a periodic input signal having a frequency which is mixed with a first frequency reference ($f_r$) resulting in a signal comprising at least two tones;

transmitting said transmitting signal through said object and medium;

receiving the resulting transmitted signal through the medium resulting in a received signal ($R_x$) wherein said received signal comprises a phase shift ($\varepsilon_0$);

characterized in that the received signal ($R_x$) comprising a phase shift ($\varepsilon_0$) is mixed with the first frequency reference ($f_r$) resulting in that the transmitting signal ($T_x$) and the received signal ($R_x$) share the frequency reference ($f_r$).

In another aspect, the present invention also relates to a device for characterizing a medium, said device comprising:

at least one means for transmitting a signal through the medium;

at least one means for receiving the transmitted signal through the medium;

a digital platform, and a data acquisition device.

Embodiments of the present invention provide sensors, inline systems or handheld systems, wherein the sensor comprises a plurality of means for generating a transmitting signal and receiving means, transmitters, receivers, digital platforms and data acquisition devices, wherein said sensor can evaluate several test samples. In alternative embodiments a plurality of transmitters and receivers may be provided, wherein they share processing means, such as a digital platform and/or data acquisition device.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 1A illustrates an embodiment of the present invention defining a signal pathway where a transmitting means and receiving means, e.g. a transmitter and receiver respectively, are positioned opposite each other defining an opening D, in which an object, like for instance a test sample, is provided. FIG. 1B illustrates an alternative embodiment of the present invention defining a signal pathway where the transmitter and receiver are positioned adjacent to each other and further comprising at least one reflector, wherein the reflector and transmitter or receiver define an opening D', in which an object, like for example an object, e.g. a test sample, medium is provided.

Figure 1A:
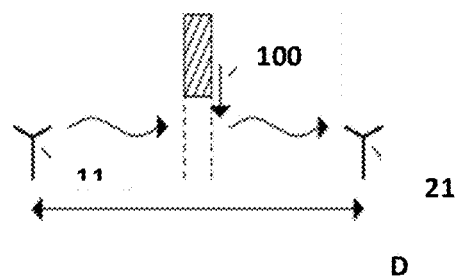
FIG. 1A and FIG. 1B schematically illustrate a signal pathway provided by a device comprising a transmitter and receiver according to embodiments of the present invention.

The drawings are only schematic and are non-limiting. In the drawings, the size of some of the elements may be exaggerated and not drawn on scale for illustrative purposes. Any reference signs in the claims shall not be construed as limiting the scope. In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to "through", reference is made to moving in one side and out of the other side of an object. In embodiments this may refer to a signal which goes through an object or in other words where sufficient amount of power is transmitted through an object in a medium and wherein the medium enables the latter (e.g. is not 100% reflective).

Where in embodiments of the present invention reference is made to "object", reference is made to objects comprising materials which are preferably sheet-like, for example a web-based sheet or a dense sheet. Also layers of biological materials can be characterized. Moreover, reference is made to, but not limited to, materials which are adapted to transmit optical signals and thus are, at least partially, transparent for optical signals. In preferred embodiments said optical signal is an electromagnetic signal. In preferred embodiments an object is capable or adapted to be partially transparent for light and/or electromagnetic waves.

The term microwaves designate the electromagnetic (EM) frequency spectrum occupying the range between 3 MHz and 300,000 MHz (300 GHz). The upper decade of this band with wavelengths below 1 centimeter is referred to as millimeter wave region. Penetration of electromagnetic energy inside an object, for example comprising dielectric media, and its sensitivity of minute changes in material medium coupled with availability of relatively large bandwidths are of great significance for nondestructive evaluation applications of millimeter wave system. Both macroscopic and microscopic properties such as density, homogeneity, for example, internal flaws, structure, porosity, moisture content, state of cure, and molecular structure have been examined in materials in solid, liquid and gaseous phase. Interaction of EM field with the medium in general takes place either with conduction electrons or with molecular dipoles resulting in attenuation and phase variation of the traveling wave. The electrical properties of non-magnetic material media can be described in terms of the constitutive parameter $\varepsilon_r = \varepsilon'_r - j\varepsilon''_r$, referred to as the relative complex dielectric constant. This quantity once measured based on the change in the through transmitted radiation, can provide accurate information about the electrical properties of the medium and subsequently be related to various material characteristics. Furthermore, polarization dependency of a coherent electromagnetic wave can provide information about orientation related properties, for example, orientation of internal flaws or fiber reinforcements in composites.

Where in embodiments of the present invention reference is made to "terahertz", reference is made to electromagnetic waves within a designated band of frequency from 0.3 to 3 terahertz (THz, where 1 THz=1e12 Hz). Wavelengths of radiation in the terahertz band correspondingly range from 1 mm to 0.1 mm (or 100 µm). Because terahertz radiation begins at a wavelength of one millimeter and proceeds into shorter wavelengths, it is sometimes known as the submillimeter band, and its radiation as submillimeter waves.

It is to be noted that where in embodiments of the present invention reference is made to a means for generating a transmitting signal, reference may be made to a transmitting signal generator, where reference is made to a means for transmitting, reference may be made to a transmitter, where reference is made to a means for receiving, reference is made to a receiver.

All embodiments described in the present invention can be used interchangeably with millimeter waves or terahertz waves. As millimeter waves exhibit significantly longer wave lengths than optical light beams, they advantageously hardly face any scattering on rough surfaces. Furthermore, millimeter waves are robust when facing fog, dust and changing light conditions.

Where in embodiments of the present invention reference is made to "electrical length", reference is made to the length of a transmission medium expressed as the number of wavelengths of the signal propagating in the medium. For instance, electromagnetic waves propagate more slowly in a medium than in free space, so a wave traveling through a medium will cover a larger number of wavelengths than a wave of the same frequency propagating over the same distance in free space. Alternatively put, one medium can be physically longer than another medium.

However, a situation can happen where the second medium is electrically longer than the first one. In preferred embodiments the invention provides a method and device which is enabled to measure the electrical length. If we know the electrical properties of a medium, then we can extract the physical length from this electrical length. We can do this using the following formula:

$$\text{electrical length} * \lambda = \text{physical length} \quad (\text{Eq. 1})$$

wherein λ is the wavelength of the frequency in the medium for which the electrical and/or physical length is measured. As a result, in order to retrieve the physical length, we need to know the wavelength (λ) of the wave. This can be calculated as follows: $c=\lambda*f$, wherein c is the speed of light in the medium. Advantageously in embodiments of the invention f is known, as f is the frequency of the carrier which is applied. If we know the speed of light in the medium (i.e. the electrical property of the medium), then we know λ and thus the physical length. Knowledge of this speed of light in the medium is required to retrieve the physical length.

Figure 1B:
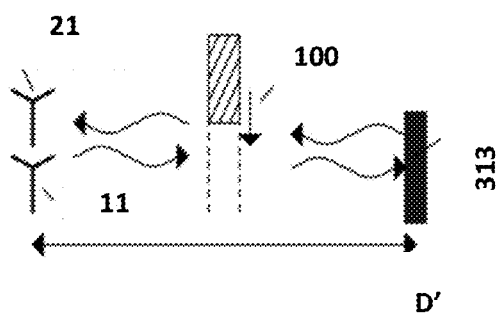

FIGS. 1A and 1B schematically illustrate a signal pathway of a sensor according to embodiments of the present invention. FIG. 1A illustrates an embodiment where a means for generating a transmitting signal 11 and receiving 21, e.g. antennas, are positioned at opposite sides defining an opening (D), where in-between an object, like e.g. a test sample, can be provided. In embodiments a sensor may further comprise a transmitter and receiver (not shown), connected to the means for generating a transmitting signal and receiving means respectively, wherein said transmitter and receiver comprise electronics of said means for generating a transmitting signal and receiving means. In preferred embodiments only said means for receiving and transmitting are to be placed in the vicinity of a medium or object in a medium of interest and not necessarily the transmitter and/or receiver. In embodiments the means for generating a transmitting signal/receiving means and transmitter/receiver may be provided as a single unit or device, wherein the means for generating a transmitting signal and transmitter and means for receiving and receiver are connected. In alternative embodiments, the means for generating a transmitting signal and transmitter may be provided on separate carriers (e.g. whereas the means for generating a transmitting signal/receiving means is provided on a frame and the transmitter/receiver is provided in a separate processing container, but where the means for generating a transmitting signal/receiving means and transmitter/receiver are connected, for example via a cable or wirelessly).

The means for generating a transmitting signal 11 is adapted to emit or transmit radiation in the EM field, whereas the means for receiving 21 is adapted to receive radiation in the EM field. The opening or gap D is representative of the electrical length without an object. The means for generating a transmitting signal 11 and receiving 21 may comprise a transmitting and receiving end respectively, such that when provided at opposite sides, the ends are pointed towards each other and substantially along a common axis. As illustrated, a signal pathway is provided when a transmitter generates a signal and transmits a signal through the means for transmitting, which goes through a medium or an object 100 (e.g. a test sample) in the medium when provided in the signal pathway, which is then received by the means for receiving and further processed by the receiver. When an object is inserted in the signal pathway the electrical length is increased, however the gap opening D remains fixed. FIG. 1B illustrates an alternative embodiment of the invention, where the means for generating a transmitting signal 11 and means for receiving 21 are positioned adjacent to each other. The means for generating a transmitting signal and receiving means may comprise a transmitting and receiving end respectively, such that when provided adjacent to each other, the ends are pointing in a same direction. In embodiments the means for generating a transmitting signal and receiving means may be antenna comprising a flared end. As illustrated by the signal pathway, a signal, after being processed in a transmitter (not shown), is transmitted by the means for generating a transmitting signal 11, which goes through a test sample 100 when provided in the signal pathway, which then is reflected by providing for example at least one reflecting means 313, wherein the means for generating a transmitting signal/receiving and the at least one reflector in addition define an opening (D'). The reflected signal, in both embodiments (FIGS. 1A and 1B), is then received by the means for receiving. In both embodiments the received signal, obtained at the receiver side, is obtained after going at least partially through the object 100 (e.g. test sample) and the medium in which the test sample is provided. Therefore, embodiments of the present invention can advantageously provide thickness and/or weight information of the test sample and/or information of the medium and/or information of the environmental parameters in which the object is provided.

In preferred embodiments of the present invention the opening (D, D') defined by the means for generating a transmitting signal and receiving means, and optionally at least one reflector, is between 10 to 60 cm, and more preferably higher than 60 cm. In preferred embodiments the object is provided in between the means for generating a transmitting signal and receiving or in between the means for generating a transmitting signal/receiving means and reflector, and more preferably in the middle, at substantially an equal distance between the means for transmitting and receiving or between the means for transmitting/receiving and reflector.

In embodiments of the present invention the transmitted signal preferably is provided by using a periodic baseband input signal having a frequency which is mixed with a first frequency reference ($f_r$), by for example a transmitter, resulting in a signal comprising at least two tones. In further preferred embodiments the transmitted signal comprises an up-converted or up-mixed signal. The transmitting signal is then transmitted through the medium or the object or the object in the medium. Then the transmitted signal, which is transmitted through the object, the medium or the object in the medium, is received resulting in a received signal ($R_x$) wherein said received signal comprises a phase shift ($\varepsilon_0$). In preferred embodiments the received signal ($R_x$) comprising a phase shift ($\varepsilon_0$) is mixed with the first frequency reference ($f_r$), by for example a receiver, resulting in that the transmitting signal ($T_x$) is generated with and the received signal ($R_x$) is processed by the same frequency and therefore share the first frequency reference ($f_r$). In a final step, the phase shift ($\Phi_0$) is estimated and related to the object's specification such to estimate the objects specification.

Figure 2:
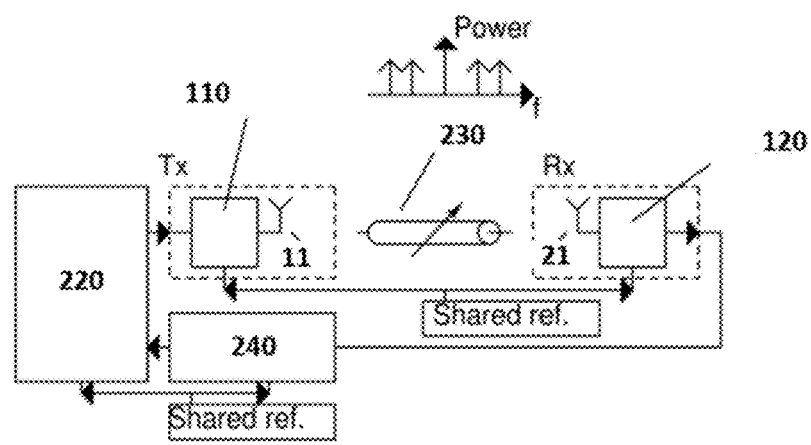
FIG. 2 schematically illustrates a block diagram of a measurement system according to embodiments of the present invention.
Figure 3:
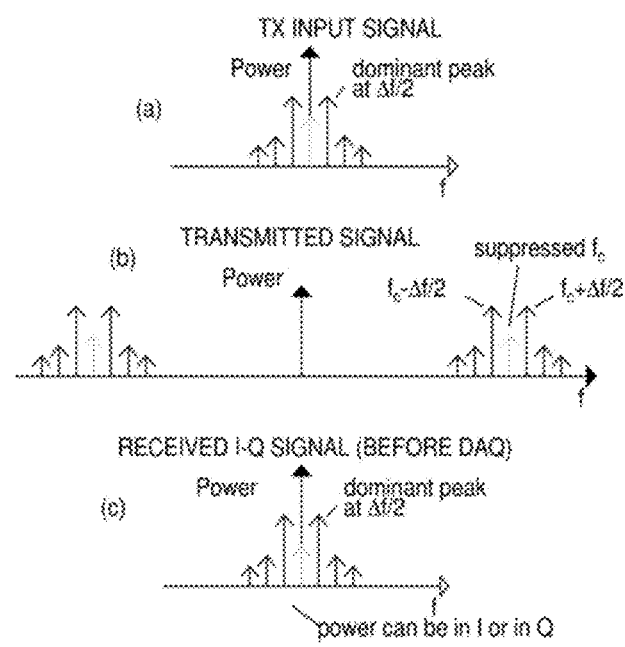
FIG. 3 illustrates on top a periodic baseband input signal used for generating a transmitting signal ($T_x$), in the middle a transmitting signal ($T_x$) is illustrated and on the bottom the periodic baseband output signal, e.g. transmitted signal received at the receiver ($R_x$) and after down conversion, according to embodiments of the present invention.
Figure 4:
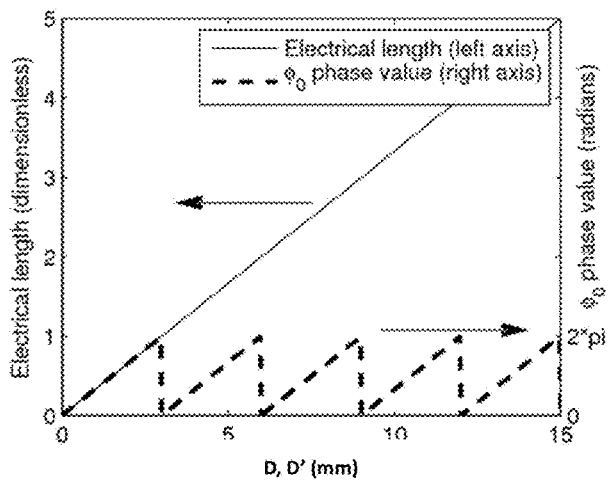
FIG. 4 illustrates a relation between an electrical length, physical length and a phase shift ($\varepsilon_0$) where the distance (D, D') between the transmitter and receiver is changed in a vacuum as medium according to embodiments of the present invention.

FIG. 2 schematically illustrates an instrument setup, which may enable a sensor according to embodiments of the present invention having a signal pathway as illustrated in FIG. 1A (cf. without reflecting means). FIG. 2 provides a general block diagram of an instrument setup according to embodiments of the present invention. An instrument setup preferably comprises: a digital platform 220, a data acquisition device (DAQ) 240, means for transmitting 11, a transmitter 110, wherein said transmitter 110 and means for generating a transmitting signal 11 enable processing and transmitting signal ($T_x$), means for receiving 21 and · a receiver 120, wherein said means for receiving 21 and receiver 120 enable receiving and processing said received signal ($R_x$). In preferred embodiments the means for generating a transmitting signal and receiving means may include antennas. The means for generating a transmitting signal and receiving means further define a channel 230, wherein the channel 230 is a representation of the opening (D) between the means for generating a transmitting signal and receiving means comprising a medium or an object e.g. a test sample, in said medium. In embodiments the means for generating a transmitting signal 11 and receiving means 21 in addition may comprise or be connected to, electronically or wireless, the transmitter 110 and receiver 120, wherein said transmitter and receiver comprising transmitting and receiving processing means, e.g. electronics, respectively. In preferred embodiments the electrical length of the channel 230 (with distance D) can be mechanically tuned, like e.g. wherein the opening (D) is changed in length. The latter is schematically depicted in FIG. 2 by the tunable transmission line symbol 230. A transmitted signal, e.g. comprising an up-converted at least two-toned signal, is preferably wirelessly transmitted through the channel. A digital platform is preferably provided to generate a baseband input signal, for example a periodic signal, which is then processed by a transmitted before transmitting said signal through the means for generating a transmitting signal. In other embodiments a digital platform, e.g. an oscillator, may be provided to generate a baseband input signal. The digital platform or oscillator preferably generates a periodic baseband input signal having a significant frequency contribution at frequency $\Delta f/2$ (see FIG. 3 (a)). This input signal is preferably fed to the transmitter 110 ($T_x$) wherein it is up converted to a millimeter-wave or terahertz band signal, by mixing the input signal with a first frequency, preferably a shared reference frequency, for example wherein the shared reference frequency may be the carrier frequency $f_c$. Note, that this up conversion may be not full-quadrature. Instead, for example only a single mixer may be used. The result of said up conversion is at least a two-toned signal having power at frequencies $f_c+\Delta f/2$ and $f_c-\Delta f/2$ (see FIG. 3 (b)). The transmitter wirelessly transmits the at least two-toned signal, via the means for generating a transmitting signal 11 which is connected to the transmitter 110, along a signal pathway as illustrated in FIG. 1A or 1B through a medium and/or an object in a medium. A time-shifted version of the signal will be detected at the receiver's end. The reason is the delay by the medium and/or object through which the signal travels. This is uniquely related to the electrical length of the medium and/or object. Once the receiver receives the up converted time-shifted signal, directly or indirectly through the at least one reflector, via the means for receiving 21 which is connected to a receiver 120 and the receiver down converts the received signal into both an in-phase (I) and quadrature (Q) component, which are provided respectively through an I-channel and Q-channel as illustrated in FIG. 3 (c). The down conversion is preferably realized by a quadrature mixing by the same first frequency or shared reference frequency, like e.g. the carrier frequency ($f_c$). Two mixers are preferably applied to enable the mixing. The electrical length of the medium is preferably derived from amplitude values of either: the I-channel, the Q-channel or a combination of I-channel and Q-channel. FIG. 4 illustrates a relation between an electrical length (solid line, left hand y-axis), physical length and a phase shift ($\varepsilon_0$) (dashed line, right hand y-axis) where the distance (D, D') between the means for generating a transmitting signal and receiving means is changed in a vacuum (as medium) according to embodiments of the present invention.

In preferred embodiments both the transmitter ($T_x$) and receiver ($R_x$) share the same timing information, so they preferably share the same frequency reference (like e.g. a carrier frequency $f_c$). In a practical implementation, this means that either the transmitter or receiver share the same source of oscillation performing the up conversion in the transmitter ($T_x$) and down conversion in the receiver ($R_x$), or that the transmitter ($T_x$) and receiver ($R_x$) use two different sources of oscillation that are phase-locked with respect to each other to perform the up- and down conversion according to embodiments of the invention. It is an advantage of embodiments of the present invention that a shared or same frequency reference provides a reliable sensor value. It is a further advantage of embodiments of the present invention that possible drift in measurements is reduced to a minimum since frequencies for the up and down conversion cannot drift with respect to each other, which reduces calibration overhead.

To obtain a practically useful resolution of the electrical and/or physical length measurement problem, the frequency of this shared reference is preferably high. With a wavelength ranging from 10 mm down to 1 mm, sub-millimeter electrical and/or physical length estimation accuracy can be achieved with millimeter wave frequencies (e.g. in the range of 30 to 300 GHz). Any frequency in this band can be used as a reference frequency for the proposed measurement system. Moreover, frequencies higher than 300 GHz, which are generally referred to as terahertz waves are also preferred for embodiments of the present invention.

If one assumes no other signal than the at least two transmitted tones is present at the receiver's front-end, the working of a sensor of the present invention can be described as follows: Let A be a value proportional to the amplitude of both the lower ($f_c - \Delta f/2$) and upper ($f_c + \Delta f/2$) dominant spectral peaks, wherein $f_c$ is the carrier frequency. Note that these peaks are spaced by a frequency of $\Delta f$. Due to the electrical length of the medium, up and down conversion is not performed on the same waveforms s(t). Instead, the waveform has undergone a time shift of $\Delta t$, yielding $s(t-\Delta t)$. t represents the time.

$$s(t-\Delta t)=A\cdot\cos(2\pi(-\Delta f/2+f_c)\cdot(t-\Delta t))+A\cdot\cos(2\pi(\Delta f/2+f_c)\cdot(t-\Delta t)) \quad \text{(Eq. 2)}$$

Let $\text{ref}_{up}(t)$ be the reference frequency for the non-quadrature up conversion in the transmitter ($T_x$) and $\text{ref}_{down}(t)$ the reference frequency for the quadrature down conversion. If one assumes the following:

$$\text{ref}_{up}(t)=\cos[2\pi f_c\cdot t], \quad \text{(Eq. 3)}$$

then taking into account a fully quadrature reference for down conversion according to embodiments of the present invention, the reference frequency for the down conversion can be expressed as follows:

$$\text{ref}_{down}=\exp(I\cdot 2\pi f_c\cdot t). \quad \text{(Eq. 4)}$$

where I is the imaginary unit.

This time-shift $\Delta t$ can be expressed as a phase shift $\Phi_0$, satisfying the following conditions:

$$\Phi_0=\text{mod}(-2\pi f_c\cdot\Delta t, 2\pi). \quad \text{(Eq. 5)}$$

In the latter expression, mod(x, y) stands for the modulo operator. The relation between electrical length, physical length and the phase shift $\Phi_0$ is visualized in FIG. 4 for the case the distance between the means for generating a transmitting signal and receiving means (D, D') is changed in a vacuum environment. Estimation of $\Phi_0$ advantageously reveals information related to the electrical length.

The received quadrature down converted signal then equals:

$$S_{received}(t)=A'\cdot\exp(I\cdot[2\pi\Delta f/2\cdot(t-\Delta t)+\Phi_0])+A'\cdot\exp(I\cdot[-2\pi\Delta f/2\cdot(t-\Delta t)+\Phi_0]) \quad \text{(Eq. 6)}$$

Wherein A' is a proportionality constant. FIG. 3 (b) shows the spectrum of the quadrature down converted signal. The two dominant peaks represent the expression of Eq. 6.

Taking respectively the real and imaginary parts of this complex received signal yields both in-phase and quadrature received signals, I and Q respectively:

$$S_{received}\,I(t)=2\cdot\cos(2\pi\Delta f/2\cdot(t-\Delta t))\cdot\cos\Phi_0\cdot A' \quad \text{(Eq. 7)}$$

$$|S_{received}\,Q(t)=2\cdot\cos(2\pi\Delta f/2\cdot(t-\Delta t))\cdot\sin\Phi_0\cdot A' \quad \text{(Eq. 8)}$$

The amplitudes of both I and Q signals the can be written as follows:

$$|S_{received}\,I(t)|=|2\cdot\cos\Phi_0\cdot A'| \quad \text{(Eq. 9)}$$

$$|S_{received}\,Q(t)|=|2\cdot\sin\Phi_0\cdot A'| \quad \text{(Eq. 10)}$$

These amplitudes can then be used to estimate the phase $\Phi_0$:

$$\Phi_0=\text{acos}(|S_{received}\,I(t)|/2A') \quad \text{(Eq. 11)}$$

$$\Phi_0=\text{asin}(|S_{received}\,Q(t)|/2A') \quad \text{(Eq. 12)}$$

$$\Phi_0=\text{atan}(|S_{received}\,Q(t)|/|S_{received}\,I(t)|) \quad \text{(Eq. 13)}$$

A' increases monotonically with increased received signal powers. The measurement should preferably not be dependent on the received power. Therefore, estimation of $\Phi_0$ is preferably done based on the atan-formula provided in Eq. 13. Using the atan-formula, the estimate is not a function of A'.

As shown in FIG. 4, $\Phi_0$ is related to the electrical length of the medium. When $\Phi_0$ is allowed to vary within a limited range, it is one-to-one related to the electrical length of the medium. Note, due to the fact that information related to the sign of $\cos(\Phi_0)$ and $\sin(\Phi_0)$ has been lost, the estimated phase $\Phi_0$ is subjected to a ambiguities. If the atan-formula of Eq. 13 is used, we see a $\lambda/4$-ambiguity or $\pi/2$-ambiguity. If either the acos-formula or asin-formula is used, we see a $\lambda/2$-ambiguity or $\pi$-ambiguity.

Figure 5:
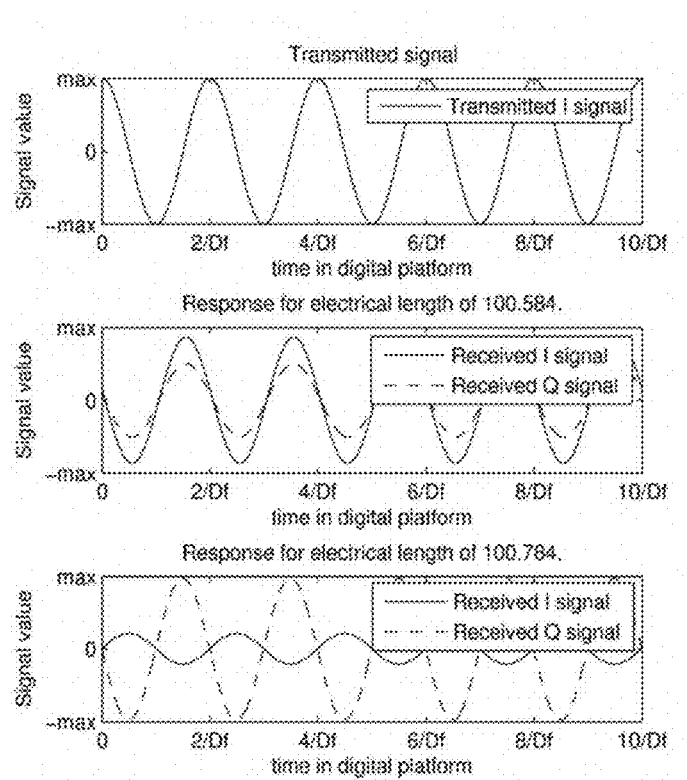
FIG. 5 illustrates a periodic baseband input signal at the transmitter (figure on top) and the corresponding periodic baseband output signal at the receiver side for two different electrical lengths (figure in the middle and bottom) according to embodiments of the present invention.

FIG. 5 shows the baseband signals, both at transmitter ($T_x$) and receiver ($R_x$) side, for two different electrical lengths. The top figure of FIG. 5 illustrates a periodic baseband input signal, where the middle and bottom figures illustrate the response signals (baseband output signal, and thus after down conversion) at receiver side for an electrical length of 100.584 and 100.784 respectively. The solid lines illustrate the received baseband output I signal, whereas the dashed lines illustrate the received baseband output Q signal. It advantageously clearly shows the high sensitivity of the amplitudes of the received I and Q signals to a changing electrical length. The I and Q amplitudes allows one to calculate an estimate for $\Phi_0$ or the electrical length of the medium. The carrier frequency ($f_c$) in this embodiment is preferably set at 60 GHz. $\Delta f$ is 2 GHz in this example. Note that in the x-axis of FIG. 5 "Df" represents $\Delta f$. Note that the presence of $\Delta t$ in the received signal enables another way to measure the electrical length. However, electrical length estimation based on estimation of $\Delta t$ is much less precise than based on estimation of $\Phi_0$.

In the following an estimation of a thickness of an object as specification of an object, for example of a dielectric object, according to embodiments of the invention is provided. The phase $\Phi_0$ or an electrical length of a medium can be related to the thickness $\delta$ of a dielectric object that is put in the medium in the signal pathway between transmitter and receiver. The index of refraction $n_{material}$ of the material in which the object is realized is known. Although sensing the thickness of objects is an important field of applications, the invention does not merely restrict itself to applications of this kind. Linking or relating the estimated $\Phi_0$, obtained by embodiments of the present invention, to an object's thickness requires an adequate model. This model can either be a mathematical expression or an empirically-obtained look-up table. If one assumes a setup as indicated in an embodiment of the invention as illustrated in FIG. 1A, where no reflector is present, one may in addition assume that reflections on the surface of the boundaries between vacuum (or air) and the object are negligible. This assumption is valid in either of the following cases: the material has an index of refraction $n_{material}$, close to 1; losses in the dielectric material are significant. The phase $\Phi_0$ related to the electrical length of the medium through which the waves or signal pass is a function of two contributions: the phase contribution due to propagation in the environment (e.g. air or vacuum) and the phase contribution due to propagation in a test object having thickness δ. Mathematically this may be written as follows:

$$\Phi_0=(2\pi(D-\delta)\cdot f_c)/c_0+(2\pi\delta\cdot f_c\cdot n_{material})c_0 \quad \text{(Eq. 14)}$$

Where D is the distance between the means for generating a transmitting signal and receiving and $c_0$ the speed of light in vacuum. If the latter would be applied for the setup as illustrated in FIG. 1B D would then be replaced by 2D' and δ by 2δ, as in that setup, the wave travels twice through the object (as can be derived from FIG. 1B). When one solves Eq. 14, one can obtain δ which is a function of $\Phi_0$ $$\delta=(c_0\Phi_0-2\pi\cdot f_c\cdot D)/(2\pi f_c\cdot[n_{material}-1]) \quad \text{(Eq. 15)}$$

As a result, an implementation of a technique for material thickness characterization based on a transmission measurement is provided. The model in this example which is used is a simple first-order model, however embodiments of the present invention is not restricted to usage of this simplified model. More complex models can be used, which can advantageously provide a more accurate view on the object's thickness. In embodiments, if the material's density is known, then, the object's thickness can be related to the weight of the material. The approach for material thickness sensing using Eq. 15 assumes that the value of $n_{material}$, the refractive index of the material for the applied waves, is known. If not known, the sensor using the sensor concept would suffer from both a sensitivity to the material's thickness δ as for its value of $n_{material}$. This so-called cross-sensitivity to both thickness and material property ($n_{material}$) can be exploited for characterization of foams, meaning both for characterization of its thickness and its weight. Experiments showed that $n_{foam}$ is a sufficient weighed average between $n_{gas}$ and $n_{polymer}$, with their weights proportional to its volume fraction in the foam material. $n_{gas}$ is the refractive index of the foam's gas. $n_{polymer}$ is the refractive index of the foam's solid material, commonly a polymer. $n_{foam}$ therefore is a monotonic function of the foam's weight. Combination of the device's measurement with for example a thickness sensor (e.g. contact-caliper), can enable the device to sense foam weights. Apart from contact-calipers several other techniques (not limited to the techniques as listed here) can be applied to assist in measuring the object's thickness: laser triangulation, ultrasound, the here-presented invention but applied using a different carrier frequency, etc.

Due to second-order effects it is however possible that the linear relationship between the electric length and the detected phase $\Phi_0$ is limited. In such a case, the electrical length of the medium without an object inserted in the signal pathway may be calibrated or tuned to work in its operating point where linearity is at its maximum. Therefore, careful calibration or tuning of the reference phase value is provided according to preferred embodiments of the present invention. The latter can be enabled using various embodiments, like for instance:
(1) tuning the delay of the transmitted signal electrically within the transmitter, which for example can be done by a phase shifting circuit;
(2) tuning the delay of the received signal electrically within the receiver. This can be done by a phase shifting circuit; and/or (3) tuning the total distance between means for generating a transmitting signal and receiving means (D, D') mechanically and optionally angular tuning can also be performed where the angle of a signal path can be fine-tuned to an optimal value such to prevent reflections towards the means for generating a transmitting signal.

Tuning a total distance between the means for generating a transmitting signal and receiving means (D) or the means for generating a transmitting signal/receiving means and reflector (D') can for example be achieved in two possible ways either by tuning the means for generating a transmitting signal-receiving means distance (D) directly, when using the instrument setup illustrated in FIG. 1A, where the means for generating a transmitting signal and receiving means are positioned opposite each other, and no reflector is used. In embodiments where a reflector is provided, like in FIG. 1B where the means for generating a transmitting signal and receiving means adjacent each other, one changes the position of the reflector and thus D' for tuning purposes. The latter embodiments have an additional advantage that the means for generating a transmitting signal and receiving means can be kept static and only the at least one reflector has to be moved. The tuning can be done manually (by for example human interaction), or being part of an automatic control system, keeping the sensor in a specific operating point. The latter is particularly interesting if ultra-high linearity is required. However, it increases the response time of the device in a way that it is only suitable for applications where measurement speeds requirements are less stringent.

An advanced possible approach of sweeping and tuning of the distance (D or D') results in a more optimal situation in which the device is fully-calibrated. Whereas the 'tuning' as mentioned above discusses mechanically moving one of the components of device to an operating point in which linearity is maximized, the following approach enables the device to respond more accurately, even when linearity is poor in a specific measurement range and measurement speed requirements are stringent. However, it is at the cost of a slightly more time-consuming calibration operation. This advanced approach (full-calibration) is now discussed. Periodic execution of this full-calibration operation not only takes care of the device's linearity (caused by imperfect IQ-imbalance, near-field effects, . . . ) as is countered by the 'tuning approach' as explained above, but also counters the effects of varying temperatures, varying humidity and varying pressure. It is based on measuring the electrical length of the gap D (or D') between the means for generating a transmitting signal and the means for receiving by means of the device itself, at different (but known) values of the gap D (or D'). This is preferably done by sweeping the gap in a range [D1,D2] (technique referred to as mechanical sweep), with the gap D (the final operating point) lying somewhere in between the extreme values D1 and D2. The sweep is carried out within steps, said steps comprising a distance of a few millimeters typically (about one wavelength of the used wave). Note that for the explanation as written above D can be replaced by D' if required. The sweep is typically performed automatically and implemented by putting either the means for transmitting or the means for receiving on a linear drive unit which is on its turn driven by a motor. The device captures data while sweeping, generating a vector of measurement points ($m_{vec}$) and a vector of position-data ($p_{vec}$) read from the linear drive unit. This sweep can be carried out in both the case when an object with known object parameters is present in the gap or when nothing is present in the gap. The collected $m_{vec}$ and $p_{vec}$ values may provide important values which will are used in the actual calibration operation. In other embodiments, one may come to a usable $p_{vec}$ and $m_{vec}$ is not to sweep the gap D (or D'), but to only collect $m_{vec}$-data for a few discrete values of D (or D') (at least two) (technique of discrete displacements). These collected values can then on their turn be used in the actual calibration operation.

It should be stressed that the full-calibration approach as shown above uses data captured at varying geometrical conditions (mechanical sweep or discrete displacements). However, the full-calibration approach is not limited to varying geometrical conditions only. A similar calibration approach can be set-up using captured data at varying electrical conditions. These electrical conditions are typically realized when an electrical-delay-tuning element or an electromagnetical delay-tuning element is introduced.

Figure 16:
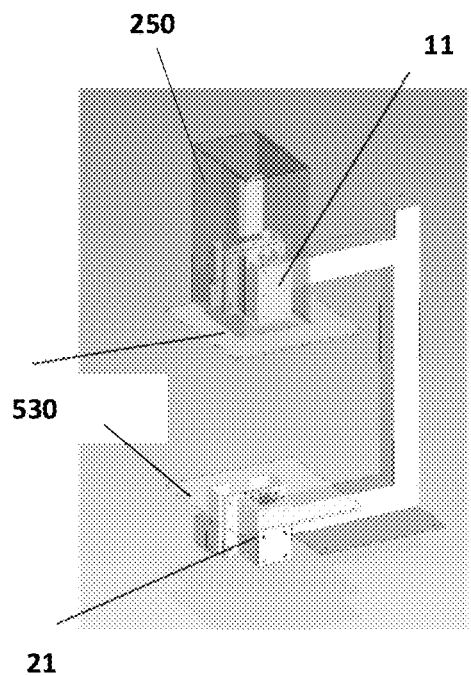
FIG. 16 shows a technical drawing showing both the transmitting and receiving means having both a sheet of radio-absorbing material applied nearby its active area.

Analysis of both the I and Q amplitudes may be performed by a computing device, preferably a field-programmable gate array (FPGA device). Depending on the sampling speed of the data acquisition device, embodiments of the present invention can be implemented in many more technologies: PCB-level electronics, laptop, full custom ASIC, DSP processors, etc. In further embodiments, the linear relationship between the electric length and the detected phase $\Phi_0$ may be increased by providing at least one radio-absorbing material nearby either the means for generating a transmitting signal or receiving means, or both. This is illustrated in FIG. 16. The technique of providing at least one radio-absorbing material also advantageously reduces the presence of possible standing waves between the transmitting and receiving means. This on its turn may possibly suppress the measurement's sensitivity to the objects position in between the two means for generating a transmitting signal and receiving means.

In embodiments the means for transmitting and means for receiving are provided and positioned such that the direction of the radiation emitted by the means for generating a transmitting signal is substantially perpendicular to the object's, e.g. sheet-like object's, surface. Alternatively, the means for generating a transmitting signal and means for receiving can be put in a way that the direction of the radiation emitted by the means for generating a transmitting signal is non-perpendicular to the material's surface. In that way, the effects of surface reflection and possible standing waves may be reduced as well. This on its turn suppresses the measurement's sensitivity to the object's position in between the two means for generating a transmitting signal and receiving means.

The analysis of the amplitudes of both I and Q signals is preferably processed in real-time on a dedicated platform. If connectivity to a host e.g. a general-purpose pc, laptop or industrial pc is required, it may be realized by an implementation of a commercially-available bus protocol. In embodiments of the present invention a USB 2.0 is used in its current state, but it is not restricted to latter. Measurement data is preferably processed by the host by either one of the following ways, for example: (a) interfacing the custom API as part of the invention, (b) interfacing the end-user graphical user interface as displayed in FIG. 6. Both methods advantageously enable measurement rates of more than 100 Hz available to the host. The host-pc may then contain a model of the dielectric object, being able to relate the detected phase $\Phi_0$ to the actual thickness or weight.

Figure 6:
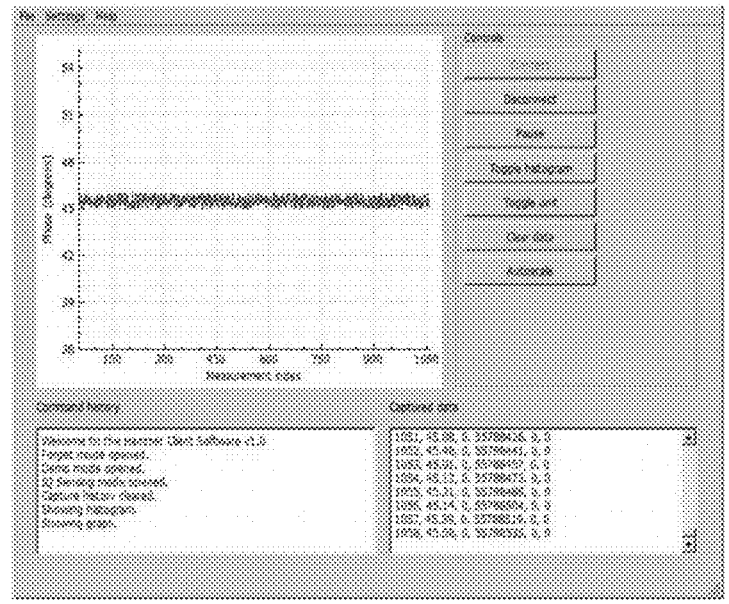
FIG. 6 illustrates an end-user graphical user interface where methods according to embodiments of the present invention have been implemented.
Figure 7:
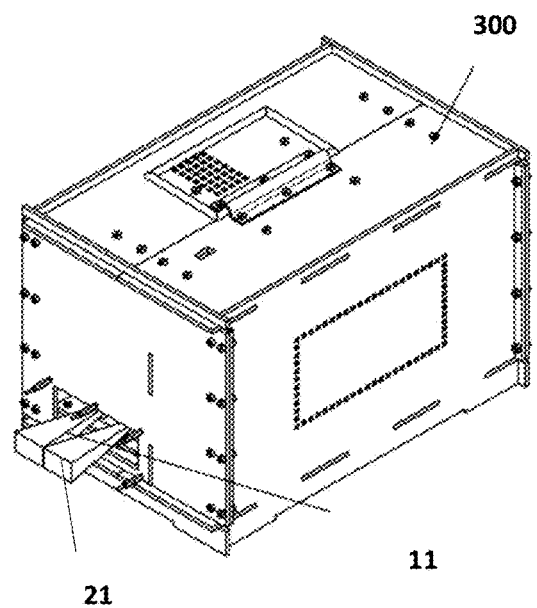
FIG. 7 schematically illustrates an embodiment of a device of the present invention.
Figure 15A:
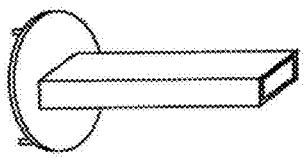
FIGS. 15A to 15C are schematic representations of alternative means for receiving or transmitting, e.g. antennas, for use in embodiments of the invention.
Figure 15B:
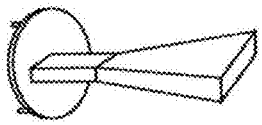
Figure 15C:
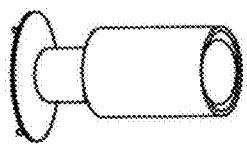

A first implementation of an instrument setup for a sensor according to the present invention is illustrated in FIG. 7 and an example of a user interface for such sensor is provided in FIG. 6. FIG. 7 schematically illustrates an enclosed a first container 300, e.g. box, comprising and more preferably containing or enclosing all electronic building blocks as provided in FIG. 2, like for example a digital platform, DAQ, a transmitter and receiver (not shown). A means for generating a transmitting signal 11 and receiving 21 are provided outside the container, e.g. on the box, adjacent to each other (analogously to FIG. 1B). The reflective means are not shown. The box is enclosed using plates and (releasable) attachment means, like for example screws, known in the art. In this embodiment the means for generating a transmitting signal and receiving means have been provided as antennas, wherein the antenna in this specific embodiment is horn-shaped and flared at the end. Depending on the application of the sensor envisioned alternative types and end shapes of antennas can be used, as illustrated schematically in FIGS. 15A to 15C. In embodiments said antenna means may be a small millimeter wave antenna or wherein said antenna means is selectively provided for the sample material. In further embodiments said antenna means is an open-ended waveguide antenna. In yet further embodiments said antenna means is a standard gain pyramidal horn antenna or a corrugated scalar horn antenna. In preferred embodiments where antennas which are horn-shaped and flared at the end are used, the latter enable one to optimally direct the power of a millimeter wave or terahertz signal in a medium and/or an object which is provided outside the container. The open end side of both antennas are provided and directed in a similar way outside of the container. The embodiment depicted in FIG. 7 is where a means for transmitting and receiving are positioned adjacent each other, having a signal path (2D') as illustrated in FIG. 1B. A device for generating a transmitting signal or receiving device used in embodiments of the present invention are preferably adapted to synthesize and wirelessly transmit millimeter or terahertz waves in a high directional way. In embodiments the transmitter, respectively receiver, may be attached to the means for generating a transmitting signal, respectively means for receiving, like illustrated in FIG. 13. In alternative embodiments the receiver, respectively transmitter, may be connected to the means for receiving, respectively means for generating a transmitting signal, by for example via a cable, wherein the receiver and the means for receiving, and respectively the transmitter and the means for generating a transmitting signal, can be separated by a distance from each other.

Figure 8:
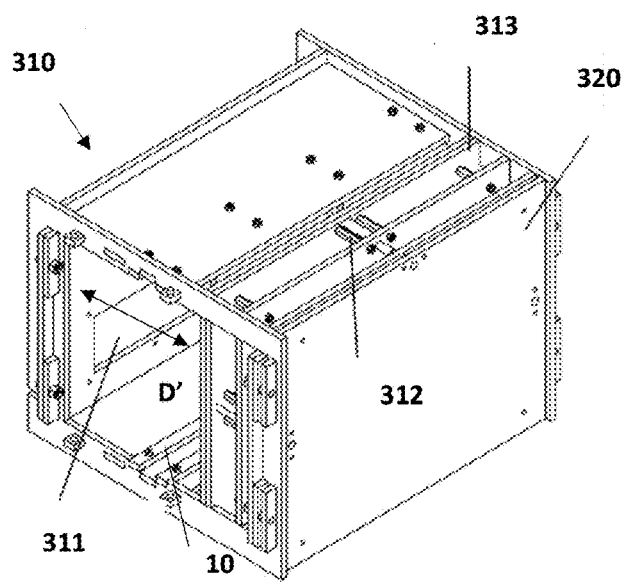
FIG. 8 schematically illustrates a box containing a reflector, said reflector comprising or consisting of a metal sheet, used in embodiments of the present invention.
Figure 9:
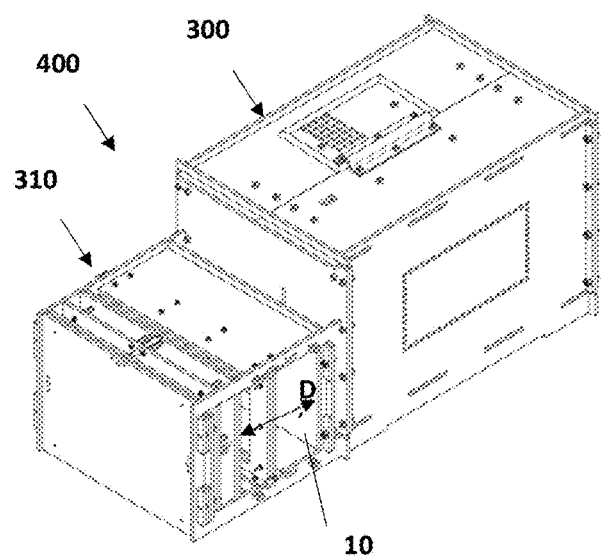
FIG. 9 schematically illustrates a device according to embodiments of the present invention, wherein the medium to be sensed is a dielectric material.

FIG. 8 schematically illustrates a second container 310, e.g. a box, comprising at least one reflecting means or reflector 313, e.g. a metal sheet. The position of the at least one reflector, e.g. metal sheet, can advantageously be tuned in order to bring the measurement in an operating point where linearity is optimal (for example by fine-tuning the opening D' using a tuning screw 312). The cavity or box 310 is configured such that it can be attached to the box comprising electronics as illustrated in FIG. 7. The rectangular opening 311, e.g. window, enables the antennas of the transmitter and receiver, which are adjacent each other and provided outside the first container 300 as illustrated in FIG. 7, to penetrate into the box as illustrated in FIG. 8. FIG. 9 shows the complete, handheld and easily transportable assembly 400, wherein the box comprising the electronics and the transmitter and receiver positioned adjacent each other 300, as illustrated in FIG. 7, is provided in a receiving box 310, for example the receiving box of FIG. 8, comprising at least an opening or window. The adjacent antennas of the box of FIG. 7 are provided in the inlet for antennas of the box illustrated in FIG. 8. An object like a test sample, for example a dielectric object, can be positioned in the cavity 10 of in the assembled box, wherein the test sample advantageously is aligned in parallel with the at least one reflector, e.g. metal reflector. In preferred embodiments the object is provided such that the direction of the radiation emitted by the means for generating a transmitting signal is substantially perpendicular to the object's surface, however as indicated earlier the present invention is not limited thereto. The assembly of FIG. 9 advantageously enables thickness/weight sensing of test samples, and more preferably dielectric sheets. The electromagnetic millimeter wave or terahertz signal, advantageously passes twice through the test sample, wherein the test sample is provided in the signal pathway 2D', such that a thickness/weight measurement is feasible. This enables a measurement precision of roughly twice as good with respect to a single transmission.

Figure 10:
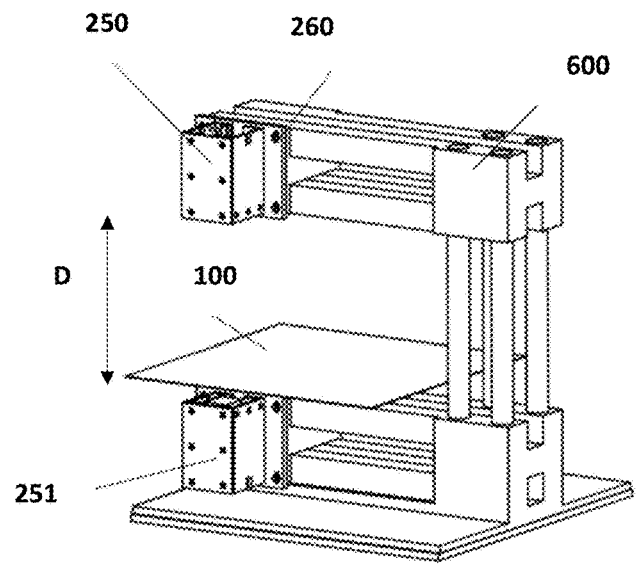
FIG. 10 schematically illustrates a device according to embodiments of the present invention, wherein a receiver and transmitter are mounted on each arm of a C-frame.
Figure 11:
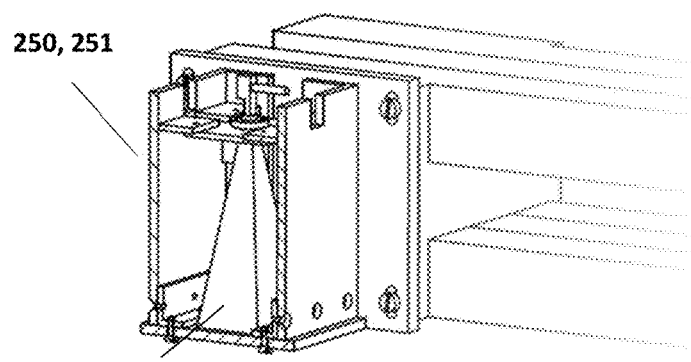
FIG. 11 schematically illustrates a carrier cage used in embodiments of the present invention.

For industrial inline measurement applications, a device as schematically illustrated in FIG. 10 may be provided. In said specific embodiment, components of a sensing device according to embodiments of the present invention may be provided on a frame 600, for example a metal frame, which in this embodiment is a c-shaped frame (c-frame). However, alternative shapes make be used a well, like for example a u-shaped (u-frame) or an o-shaped frame (o-frame). In preferred embodiments the frame is configured such that a means for generating a transmitting signal 11 and means for receiving 21 (not shown), for instance in the form of antennas, can be positioned on opposite sides of the frame, defining a distance or opening D. In embodiments a transmitter and receiver (not shown) can be provided on the frame as well, connected and attached to the means for generating a transmitting signal and receiving means respectively. In alternative embodiments, the transmitter and receiver are not provided on the frame but are connected to the means for generating a transmitting signal and receiving means respectively. In preferred embodiments this distance or opening D can be tuned by for example using a distance tuning knob 260. In such embodiments, the means for generating a transmitting signal and receiving means in the form of antennas are mounted in an opposite direction relative to each other, realizing the measurement principle as described in FIG. 1A. The opening defined by the shape of the frame is put around a test sample 100 (for example an industrial web, sheet or film), in order to enable sensing a thicknesses or weights of the test sample, for example a web. The web is referred to as "object to be measured" in FIG. 10. Note that FIG. 10 displays a c-frame solution but implementation of other frames would be straightforward for the skilled person. In preferred embodiments horn-shaped antennas are used, which are protected by protecting means 250, 251 like for example by providing them in carrier cages 250, 251, protecting them from inline harsh environments. Wherein the carrier cage preferably has openings or windows or material which are partially translucent preferably for millimeter-waves. The carrier cages are preferably realized in metal. In order to protect the inner parts of the antennas, a dielectrical window can be added to openings or windows provided in the carrier cage, advantageously sealing the carrier cage completely. FIG. 11 shows a close-up on a preferable realization of a protecting means, e.g. carrier cage (also part of FIG. 10) comprising an opening according to embodiments of the invention. Note that the drawing represents a cutted protecting means in a way that the antenna, which is inside becomes visible. The antenna in this case is a pyramidal horn. In front of the antenna's opening a dielectric window can be applied (which is not shown here) and/or radio-absorbing material 530 as illustrated in FIG. 16.

Figure 12:
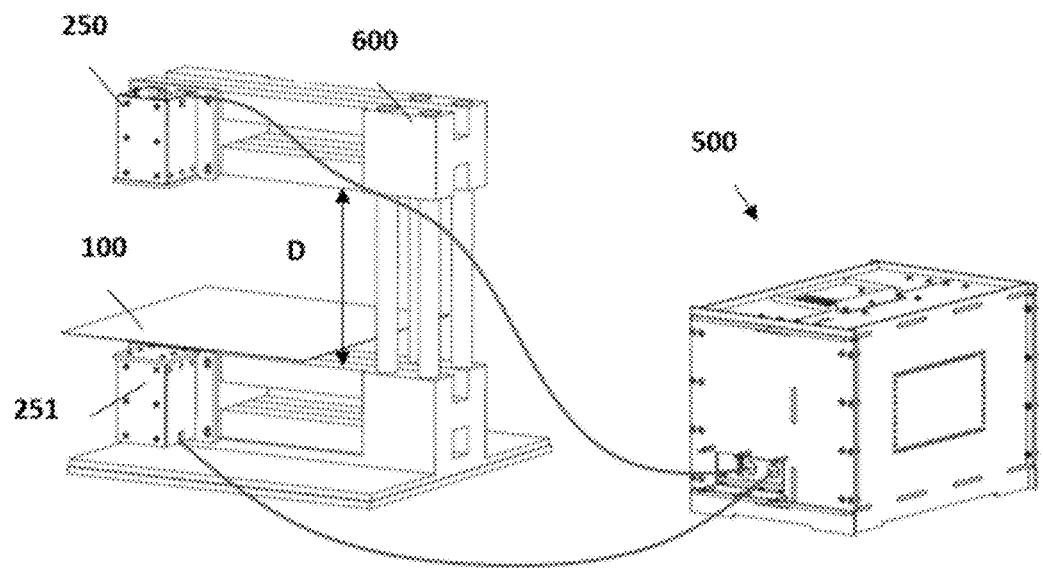
FIG. 12 schematically illustrates a device according to embodiments of the present invention mounted on a C-frame.

A total instrument setup of a sensor according to embodiments of the invention is illustrated in FIG. 12. FIG. 12 illustrates a box comprising the hardware 500, like for instance the device illustrated in FIG. 7 but without the antenna's provided adjacent to each other, wherein the device is connected to a c-frame 600 which can be used in inline set-ups, wherein the c-frame comprises the means for generating a transmitting signal 11 and receiving means 21 on opposite sides of the frame and not the box of FIG. 7 as described earlier, in order to come to a fully-integrated static inline measurement solution wherein the object to be measured is moved. In FIG. 12 the means for generating a transmitting signal and receiving means are not shown as they are protected by a carrier cage 250, 251. In addition, the distance or opening between the transmitter and receiver D may be tuned. In addition, the opening defined by the shape of the frame is put around a test sample 100. In alternative the transmitter and receiver may also be provided on the frame (via the means for generating a transmitting signal and receiving means respectively) instead of in the container 500.

Figure 13:
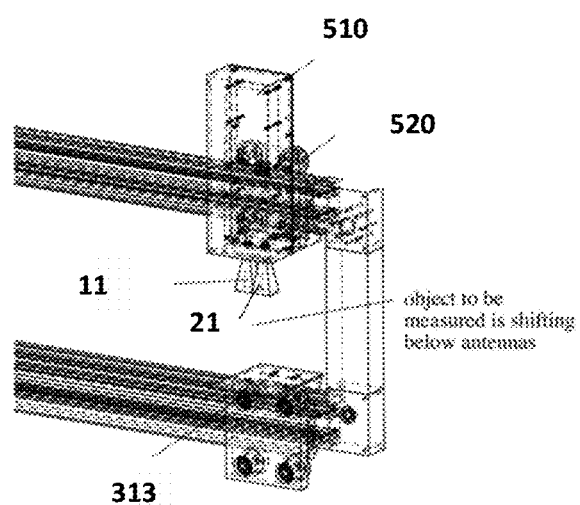
FIG. 13 schematically illustrates a device according to embodiments of the present invention wherein a receiver and transmitter are mounted on each arm of a O-frame.

FIG. 13 illustrates another embodiment of the present invention which comprises an electronic platform 510 comprising a means for generating a transmitting signal 11 and receiving means 21 in the form of flared antenna's, wherein the electronic platform is similar to the container illustrated in FIG. 7. In embodiments, the electronic platform 510 may comprise a transmitter and receiver, which are connected to the means for generating a transmitting signal and receiving means respectively and other components as illustrated in FIG. 2. The device of FIG. 13 furthermore comprises means or mechanics for enabling free translation 520 of the electronic platform 510 perpendicular to the measurement direction. In specific embodiments the electronic platform 510 can be mounted on a cart or integrated in a cart, wherein said cart is adapted to move over a frame, in various directions. A cart by Mahlo can for example be used in embodiments of the present invention, like illustrated on this link: http://www.mahlo.com/fileadmin/_migrated/pics/ Qualiscan_QMS-12_WebPro-M_2_800×600.png. If this cart is put for instance on an o or u-frame by a mechanical bearing mechanism, an industrial sample scanner, e.g. a web scanner is realized, providing an inline scanning device. In this specific embodiments, the object to be measured is moved or shifted below the means for transmitting 11 and receiving 21 in the opening defined by the frame. The flared side of the antennas connected to the transmitter and receiver are pointing in the same direction, and wherein the transmitter and receiver are positioned adjacent each other. In this embodiment a signal pathway as illustrated in FIG. 1B is enabled due to the reflector 313 used. In embodiments a reflector 313 preferably is a sheet of metal. In an alternative implementation, where no reflector used, the receiver antenna 21 can be put on the other side of the object to be measured or sensed (like e.g. a material), e.g. on the other side of the frame. In further embodiments, a carrier cage (not shown) may be provided for housing an antenna, wherein the carrier cage comprises opening, wherein said openings may be sealed by means of a dielectric window. The carrier cage can be applied around the antennas to protect the device's parts from potential inline harsh environments.

In embodiments a 60 GHz carrier frequency may be used. However, any millimeter-wave or terahertz frequency can be used to make a similar setup. Implementations are not restricted to this 60 GHz.

Figure 14:
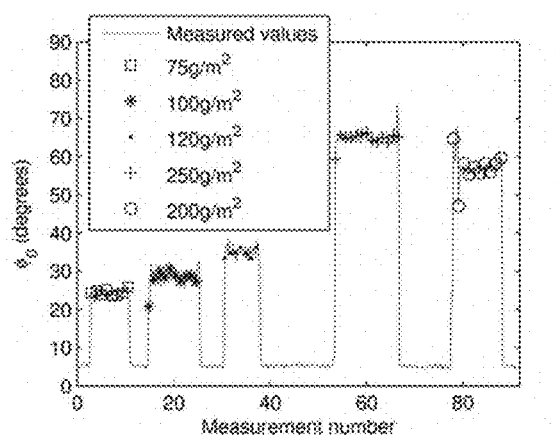
FIG. 14 schematically illustrates measurement results when for example sheets of paper are sensed using embodiments of the present invention.

FIG. 14 shows typical measurement results when different sheets of paper are provided as test samples in a sensing device according to embodiments of the invention. Paper weights vary between 75 to 250 grams per square meter. The phase shift $\varepsilon_0$ advantageously is highly sensitive to the different paper weights. Based on a model, they can be correlated to their corresponding weight value.

Figure 17:
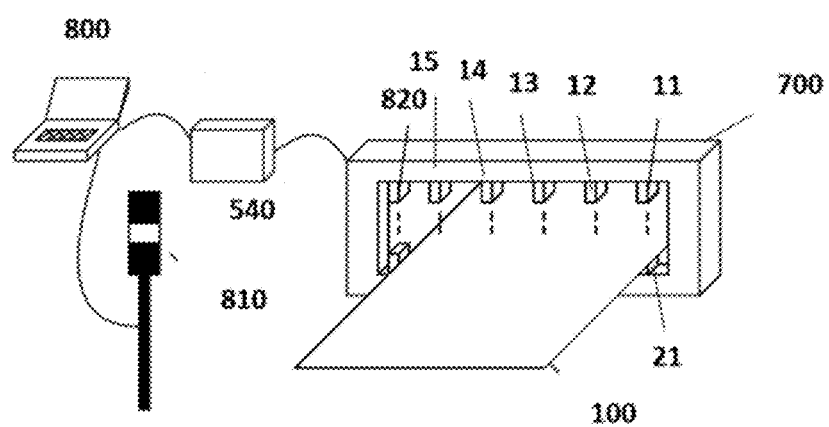
FIG. 17 schematically illustrates an O-frame comprising a plurality of receivers and transmitters provided in an array according to embodiments of the present invention.

FIG. 17 schematically illustrates an O-frame comprising a plurality of means for generating a transmitting signal and receiving means, more specifically a plurality of pairs of means for generating a transmitting signal and receiving means. For example, a device may comprise an O-frame comprising five sensor head pairs, each pair comprising means for transmitting (11, 12, 13, 14, 15) and means for receiving (21, 22, 23, 24, 25), the means for receiving 22 to 25 not shown, and each pair separated by a distance D and having a signal pathway as illustrated in FIG. 1A. The O-frame further comprises a calibration path 820 preferably provided adjacent to a sensor head pair. In preferred embodiments the plurality of means for generating a transmitting signal and means for receiving are pairwise arranged in an array. In FIG. 17 a specific embodiment of five means for generating a transmitting signal and receiving means is provided. It would be straightforward for the skilled person to implement a device comprising a reflector wherein the sensor pair are provided next or adjacent to each other (having a signal pathway as illustrated in FIG. 1B). A box comprising the hardware 540, like for instance the device illustrated in FIG. 7, but without the antenna's may be provided, which may be used and which is connected to the o-frame which is enabled to process a method according to embodiments and can be used as processing electronics. The array of sensor heads in the embodiment illustrated on FIG. 17 is provided on an o-frame, however other shapes of frames can be used as well. The set-up of FIG. 17 resembles the set-up provided in FIG. 10, but where a plurality of means for generating a transmitting signal and means for receiving pairs, separated by a distance D, are repeatedly provided next to each other, preferably over a same distance at each side. In other words, where several set-ups described as described in FIG. 1A provide one pair and wherein several pairs are provided next to each other. However, only one box 540 is provided to read-out values provided by the array of pairs of means for generating a transmitting signal and means for receiving. In embodiments of the present invention, as illustrated in FIG. 17, warning means 810 may be provided to indicate if an object being evaluated by a device has deficiencies and/or if other problems arise for example in the production line. For example, a stack light may be used a warning device 810 according to embodiments of the present invention. The entire setup may be monitored by using an industrial computer 800, which is enabled to automatically perform methods of the present invention and which may use the user interface as illustrated in FIG. 6

Figure 19A:
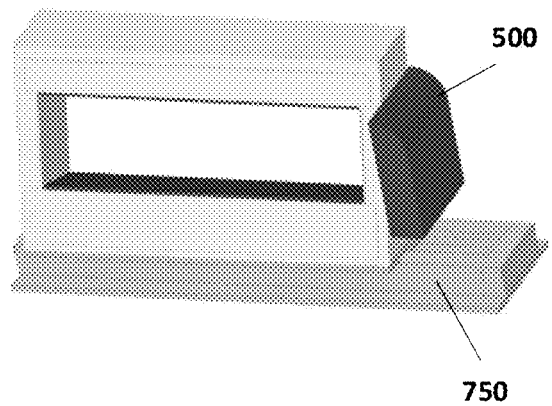
FIGS. 19A and 19B illustrate an O-frame comprising a plurality of receivers and transmitters provided in an array according to embodiments of the present invention.
Figure 19B:
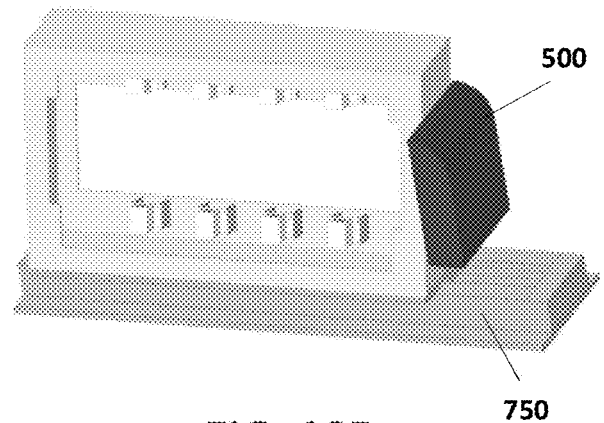

Such an O-frame containing an array of pairs of means for generating a transmitting signal and receiving means can be mounted on a linear drive unit 750, as depicted in FIGS. 19A and 19B. This creates a rigid scanning solution which enables scanning an object, like a sheet-like material, which is provided in the opening or window defined by the O-frame, over its complete width, moreover, only requiring a minimum amount of mechanical displacement. The container or box comprising the hardware, like for instance the device illustrated in FIG. 7, but without the antenna's, is provided 500, and attached to the O-frame, which in use is a moving o-frame, realizing a rigid construction where the effects of mechanical vibrations and displacements on the measurement is reduced to a minimum. Thus in use the container or box 500 comprising the hardware moves along with the O-frame. FIG. 19A and 19B depict two alternative embodiments of the present invention: a first embodiment (illustrated in FIG. 19A) illustrates one with nearly full-coverage of the pairs comprising a front-plate and a black protective sheet, preferably covered with radio-absorbing material, and a second alternative illustrated in FIG. 19B where the pairs of means for generating a transmitting signal and receiving means are directly visible.

Figure 18:
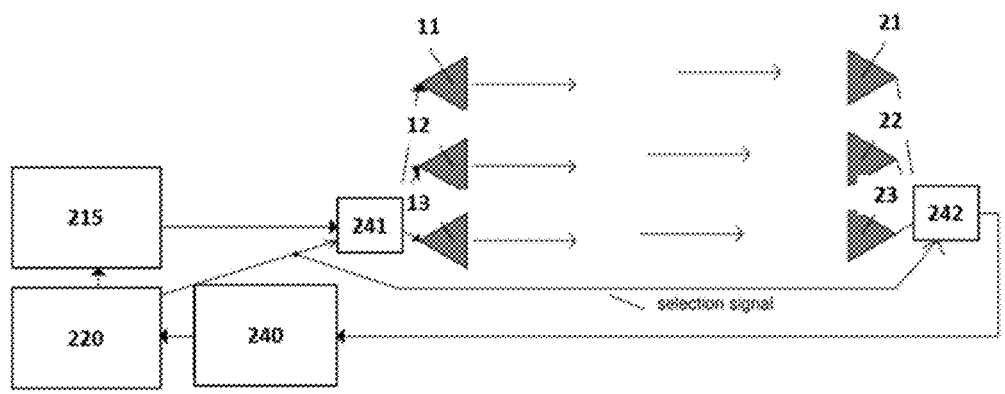
FIG. 18 illustrates a block diagram for embodiments of the present invention using an array of receivers and transmitters.

FIG. 18 illustrates a block diagram for embodiments of the present invention using an array of means of transmitting 11, 12, 13 and means of receiving 21, 22, 23, like illustrated in FIG. 17. Wherein the array comprises pairs of means for transmitting and receiving (11,21;12,22;13;23) each separated with a distance D. The block diagram illustrates a means for demultiplexing, referred to a demulitplexer (241), and a means for multiplexing, referred to as a multiplexer (242) preferably combined into one single casing. Both devices 241, 242 are applied to capture measurement data performed by different pairs of means for generating a transmitting signal and receiving means (11,21; 12,22; 13; 23) when an array configuration is realized. The demultiplexer 241 enables shutdown of all means for generating a transmitting signal (11,12,13) except for one. The multiplexer 242 enables shutdown of all means for receiving means (21,22,23) except for one by an electronic configuration. When both the multiplexer 242 and demultiplexer 241 are configured to 'select' corresponding means for generating a transmitting signal and receiving means, then, a measurement can be performed by these 'selected' means for generating a transmitting signal and receiving means. A processing unit is also provided which is connected to a single means for generating a transmitting signal and means for receiving of the array, wherein the processing comprises a signal generation device 215, a digital platform 220 and a DAQ (240). The electronic configuration of both the multiplexer and the demultiplexer may change over time, realizing measurement data from different means for generating a transmitting signal and means for receiving pairs as a function of time. Both the demultiplexer and multiplexer each are preferably implemented by means of an SPxT (single pole x-throw) millimeter wave switch, with x being the amount of means of generating a transmitting signal or means of receiving of the system. E.g. an SP4T switch enables using four means for generating a transmitting signal and four means of receiving to be installed in an array solution. Alternatively, both the multiplexer and demultiplexer can be incorporated in one single device, which is preferably implemented as a DPxT millimeter wave switch, wherein the D stands for "double".

In embodiments of the present invention calibration or tuning of the system or may be performed. Calibration or tuning of the measurement is preferably performed for every pair of means for generating a transmitting signal and receiving means. It can be done for every pair in one of the ways as described above (e.g. tuning a total distance between means for generating a transmitting signal and means for receiving (D,D')), or by taking over the calibration or tuning information from another pair (=reference pair) of means for generating a transmitting signal and means for receiving. According to embodiments this can either be done by:

1. Taking over the exact copy of the calibration information (e.g. an offset value, or a gain value, . . . ) from the reference pair, and thus assuming that all pairs face the same non-idealities that destroy their calibration state over time. This is an acceptable way of calibration whenever the requirements for precision are less stringent (when the electrical distance needs to be determined with a precision of 0.01λ or worse.)

2. Letting calibration data (e.g. an offset value, or a gain value) from the reference pair ripple over the width of the material to the specific pair that needs to be calibrated. This is preferably done by creating a structure as shown in FIG. 19. In FIG. 19, the pairs are spaced at a distance less than the stroke of the linear drive unit. Thus, there are some spots along the width of the material that are measured by two neighboring pairs. These measurement points are extremely valid for a neighbor-based calibration operation, enabling calibration of a pair relative to a pair lying closer to the reference pair, and so on . . . . All pairs can thus be calibrated using that approach.

It is to be understood that this invention is not limited to the particular features of the means and/or the process steps of the methods described as such means and methods may vary. It is also to be understood that the terminology used herein is for purposes of describing particular embodiments only, and is not intended to be limiting. It is also to be understood that plural forms include singular and/or plural referents unless the context clearly dictates otherwise. It is moreover to be understood that, in case parameter ranges are given which are delimited by numeric values, the ranges are deemed to include these limitation values.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The invention claimed is:

1. A method for estimating a specification of a medium or an object in a medium, said method comprising:
generating a transmitting signal, wherein the transmitting signal is provided by using a periodic baseband input signal having a frequency which is mixed with a first frequency reference resulting in a signal comprising at least two tones;
transmitting said transmitting signal through said object and/or medium;
receiving the resulting transmitted signal, transmitted through the object and/or medium, resulting in a received signal wherein said received signal comprises a phase shift;
wherein the received signal comprising the phase shift is mixed with the first frequency reference resulting in that the transmitting signal is generated with and the received signal is processed with the same frequency reference and therefore share the first frequency reference, and
estimating the phase shift and relating the estimated phase shift to the medium's and/or object's specification such to estimate the medium's and/or object's specification.

2. The method according to claim 1, wherein a model is used to relate the estimated phase shift to the medium's and/or object's specification, wherein the model can be a mathematical expression or an empirically-obtained look-up table.

3. The method according to claim 1, wherein the mixing of the received signal with the first frequency reference comprises converting the received signal in an in-phase and/or quadrature component.

4. The method according to claim 3, further comprising a digitizing step, wherein said digitizing step comprises digitizing the in-phase and/or quadrature component and/or comprises providing a second reference frequency.

5. The method according to claim 4, wherein said second reference frequency is equal to the first reference frequency.

6. The method according to claim 1, wherein the specification of the object estimated is at least one of the following: a thickness of the object or weight of the object or a coating thickness of the object or a parameter indicative of the di-electric state of the object and/or the refractive-index and/or dielectric constant.

7. The method according to claim 4, wherein a thickness of the object is estimated using amplitude values of the in-phase component, the quadrature component or a combination of both.

8. The method according to claim 1, further comprising a monitoring step, wherein environmental parameters of the object in which the estimation is performed are obtained.

9. The method according to claim 8, wherein the environmental parameters are pressure, temperature and/or humidity.

10. The method according to claim 1, further comprising a calibration step comprising one of:
tuning a delay of the transmitted signal electrically within a transmitter, or
tuning a delay of the received signal electrically within the receiver, or
tuning or sweeping a total distance between a signal generator arranged to generate a transmitting signal and a signal receiver arranged to receive the receiving signal mechanically, or
tuning or sweeping a total distance between the signal generator and a reflector for reflecting mechanically, or
angular tuning, said angular tuning comprising fine-tuning an angle of a signal path to an optimal value such as to prevent reflections towards the signal generator.

11. The method according to claim 1, wherein the object is a sheet material having a thickness in the micrometer to centimeter range and/or wherein the object and medium are adapted to at least be partially transparent for millimeter or terahertz waves and/or wherein the first reference frequency is in the order of 0.1 MHz to 3000 GHz, preferably 1 GHz to 300 GHz and more specifically 10 GHz to 150 GHz.

12. A computer program product for, if implemented on a control unit, performing a method according to claim 1.

13. A control unit programmed for performing a method according to claim 1.

14. The system according to claim 1, comprising a plurality of pairs of transmitting signal generators for generating a transmitting signal and receivers, wherein the plurality of transmitting signal generators and receivers are provided on a frame defining an opening which can be adjusted.

15. A system comprising:
a plurality of pairs of transmitters and receivers, wherein the plurality of transmitters and receivers are provided on a frame defining an opening which can be adjusted;
a control unit for performing a method according to claim 1.

16. A system for characterizing a medium or an object in a medium, said system comprising:
at least one transmitting signal generator configured for generating a transmitting signal provided by using a periodic baseband input signal having a frequency which is mixed with a first frequency reference resulting in a signal comprising at least two tones, for transmitting the transmitting signal through the medium or the object in the medium;

at least one transmitted signal receiver configured for receiving the transmitted signal, transmitted through the medium or the object in the medium, thus obtaining a received signal, the received signal comprising a phase shift; and a control unit programmed for mixing the received signal with the first frequency reference resulting in that the transmitting signal is generated with and the received signal is mixed with the same frequency therefore sharing the first frequency reference, estimating the phase shift, and relating the estimated phase shift to the medium's and/or object's specification such to estimate the medium's and/or object's specification.

17. The system according to claim 16, the system comprising a digital platform configured for generating a periodic baseband input signal having a frequency.

18. The system according to claim 16, wherein the at least one transmitting signal generator for generating a transmitting signal and at least one receiver for receiving are provided opposite each other defining an opening with a distance, or wherein the receiver and the transmitting signal generator are positioned adjacent each other and the system further comprises a reflector for reflecting the resulting transmitted signal, wherein the receiver and the transmitting signal generator are positioned opposite to the reflector defining an opening with a distance, or wherein the at least one transmitting signal generator and receiver are provided on a C, U or O-frame, or wherein the at least one transmitting signal generator and receiver are adapted to move in a same direction with respect to an object when in use.

19. The system according to claim 18, wherein the defined openings can be adjusted.

20. The system according to claim 16, the system comprising an O-frame comprising a plurality of sensor head pairs, each pair comprising a signal generator and a receiver, and each pair separated by a distance D.

* * * * *